(12) United States Patent
Schmucker et al.

(10) Patent No.: US 7,202,472 B2
(45) Date of Patent: Apr. 10, 2007

(54) MASS SPECTROMETRIC ANALYSIS USING NANOPARTICLES

(75) Inventors: Jürgen Schmucker, Stuttgart (DE);
Thomas Schiestel, Stuttgart (DE);
Herwig Brunner, Stuttgart (DE);
Günter Tovar, Stuttgart (DE)

(73) Assignee: Fraunhofer-Gesellschaft zur Forderung der Angewandten Forschung e.V. (DE)

( * ) Notice: Subject to any disclaimer, the term of this patent is extended or adjusted under 35 U.S.C. 154(b) by 224 days.

(21) Appl. No.: 10/488,061

(22) PCT Filed: Aug. 16, 2002

(86) PCT No.: PCT/EP02/09196

§ 371 (c)(1),
(2), (4) Date: May 10, 2004

(87) PCT Pub. No.: WO03/021267

PCT Pub. Date: Mar. 13, 2003

(65) Prior Publication Data

US 2005/0037516 A1    Feb. 17, 2005

(30) Foreign Application Priority Data

Aug. 31, 2001 (DE) ................ 101 44 250

(51) Int. Cl.
*H01J 49/00* (2006.01)
(52) U.S. Cl. .................................... 250/288
(58) Field of Classification Search ............ 250/288, 250/287
See application file for complete search history.

(56) References Cited

U.S. PATENT DOCUMENTS

| 5,922,537 A | 7/1999 | Bogle et al. |
| 6,056,877 A | 5/2000 | Taylor et al. |
| 6,277,573 B1 | 8/2001 | Koester |
| 2004/0028694 A1* | 2/2004 | Young et al. ............ 424/190.1 |

FOREIGN PATENT DOCUMENTS

| WO | 96 29431 | 9/1996 |
| WO | WO 01/25002 | 10/2000 |

OTHER PUBLICATIONS

International Search Report.
Evaluation of the variables that affect resolution in delayed extraction MALDI-TOF' (Article) By Damon C. Barbacci et al. *Elsevier Science B.V.*, 1997.
Invitrogen Online Ordering: Dynabeads M-280 Streptavidin www.catalog.invitrogen.com German Office Action dated Dec. 5, 2005.

* cited by examiner

*Primary Examiner*—Kiet T. Nguyen
(74) *Attorney, Agent, or Firm*—Ostrolenk, Faber, Gerb & Soffen, LLP (57) ABSTRACT

The present invention relates to an improved method for mass spectrometric analysis, in particular for matrix-assisted laser desorption/ionization time-of-flight mass spectrometry (MALDI-TOF MS) using nanoparticles, where an analyte is added to a nanoparticle suspension, and the suspension containing the bound analyte is then deposited directly on a MALDI sample carrier and investigated by mass spectrometry, and to nanoparticles suitable for this method.

42 Claims, 5 Drawing Sheets

MASS SPECTROMETRIC ANALYSIS USING NANOPARTICLES

BACKGROUND OF THE INVENTION

The present invention relates to an improved method for mass spectrometric analysis, in particular for matrix-assisted laser desorption/ionization time-of-flight mass spectrometry (MALDI-TOF MS), using nanoparticles, with an analyte being added to a nanoparticle suspension, and the suspension containing the bound analyte then being deposited directly on a MALDI sample carrier and investigated by mass spectrometry, and to nanoparticles suitable for this method.

Mass spectrometry is a method for elucidating the structure of substances, with atomic and molecular particles being separated according to their mass. It is based on a reaction between molecules and electrons or photons. Bombardment of the sample with electrons results, as a consequence of the elimination of electrons, in positive molecular ions which then dissociate into various ionic, free radical and/or neutral fragments. Molecular ions and fragments are separated in suitable separating systems according to the size of the mass number. Thus, mass spectrometry differs from real molecular spectrometric methods such as UV/vis, IR or NMR spectroscopy by using molecular ions and fragments resulting from chemical dissociation reactions as a consequence of an ionization process for elucidating the structure of substances.

The ions which are formed are separated according to their mass/charge (m/z) ratio in an analyzer, for example a magnetic or electric field. A mass spectrometer therefore generally consists of the following main components: the sample substance is vaporized in the inlet system and introduced in vapor form into the ion source in which the ionization takes place owing to, for example, electron impacts. The analyzer serves to separate, i.e., focus, the radical cations and cations formed in the ion source according to the mass-to-charge ratio. The substance vapor which has passed from the inlet system into the ion source is bombarded there by electrons which are emitted by an electrically heated metal wire, the filament. Between the filament and the electron target, the sample carrier, there is the so-called chamber voltage which accelerates the electrons to the desired energy.

Time-of-flight mass spectrometers have dynamic ion separation systems. In the time-of-flight mass spectrometer, ions differing in mass are separated on the basis of the differences in their time of flight for a predetermined path length. The accelerated ions enter the flight tube in which the end is reached faster by lighter than by heavier ions. Besides electron impact ionization, further ionization methods used are field ionization and field desorption ionization. In field ionization, positive ions are generated by removing an electron in a strongly electric field. Owing to the low energy of the molecular ions, only few fragmentations occur. To ionize compounds which are difficult to vaporize (field desorption ionization), a solution of these compounds is applied to an activating metal wire connected as anode. The ions resulting after application of the electric field are desorbed.

Matrix-assisted laser desorption/ionization time-of-flight mass spectrometry (MALDI-TOF MS) has developed in recent years into an important method for analyzing a wide variety of substances, especially proteins. The main advantages of this method include extremely rapid positive identification of an analyte, for example of a protein, through its mass-to-charge ratio (m/z) and the extremely low limit of detection, which is in the femtomole region or below.

Protein biochips have been developed in recent years for mass spectrometric analysis. In these, chemically functional groups are covalently tethered on the chip surface as self-assembled monolayers (SAM). Appropriately prepared proteins are attached as receptors to these systematically disposed tether molecules. Subsequently, libraries of optional binding partners are applied to the surface. Excess material is removed by using suitable cleaning steps, while specifically bound ligands remain tethered to the surface and can be analyzed directly by mass spectrometry.

There are, however, two problems in principle with the binding of tether proteins used to capture ligands on flat surfaces. A flat surface considerably restricts the amount of tether proteins which can be bound in a relatively small region, and the analyte is not efficiently aligned in relation to the solid-phase capture surface.

These problems are therefore solved by employing particulate binding matrices, since particles, especially particles in the nanometer range, have a very large surface area. Particulate systems with magnetic properties are employed in particular for high-affinity attachment, separation and preconcentration of proteins (Merchant and Weinberger, Electrophoreses, 21 (2000), 1164–1167). Sample preparation for MALDI-TOF MS analysis is common knowledge. For example, antibodies of a protein to be isolated are immobilized on the particle surface and then the corresponding protein is captured from complex matrices (Hurst et al., Anal. Chem., 71 (1999), 4727–4733). Particles which have been employed in particular are magnetic particles, polystyrene particles and Sephacryl particles. The molecules are coupled to the particles via a glutaraldehyde bridge or via a direct linkage via CNBr-activated carbohydrates.

However, it has emerged that the particulate systems employed to date are not entirely compatible with the actual MALDI analysis method and therefore must be removed before application to the sample carrier in order to avoid interference with the MALDI process. This means that the particulate binding matrices are used in order to isolate and purify analytes, but must be released again from the immobilized analytes in an additional operating step before the sample application to the MALDI sample carrier. Only then is it possible to analyze the analytes by means of the MALDI-TOF MS method.

SUMMARY OF THE INVENTION

The technical problem on which the present invention was based is thus to develop means and methods with the aid of which it is possible for analytes, especially proteins, to be isolated, purified and subsequently MALDI-TOF-analyzed, in particular avoiding the problems known in the prior part, i.e. that the means used to isolate analytes from complex matrices do not interfere with the subsequent MALDI-TOF method and therefore do not have to be removed before carrying out this method, and thus that both the sample preparation and the MALDI-TOF analysis is considerably simplified.

The present invention solves the problem on which it is based through the provision of a method for investigating at least one analyte by means of matrix-assisted laser desorption/ionization time-of-flight mass spectrometry (MALDI-TOF MS), comprising the provision of a sample with the analyte having first functional groups, the provision of nanoparticles which comprise a core with a surface which has complementary second functional groups which bind the first functional groups, the provision of a suspension of the nanoparticles in an aqueous or organic liquid, the addition of the sample containing the at least one analyte to the suspension, or the addition of the nanoparticle suspension to the sample containing the analyte, the affinity binding of the analyte to the nanoparticles, the subsequent deposition of the suspension containing the bound analyte on a MALDI sample carrier, and the spectrometric investigation of the analyte.

The present invention thus provides a method with the aid of which it is possible to prepare a sample for subsequent mass spectrometric analysis, i.e. the an analyte can be isolated from a sample and be separated from other components of the sample and subsequently be investigated by means of matrix-assisted laser desorption/ionization time-of-flight mass spectrometry (MALDI-TOF MS). This entails a suspension of nanoparticles whose surface has functional groups specifically matched to the analyte being added to the sample which contains the analyte, which may be for example an unpurified biological fluid, or the sample containing the analyte being added to the nanoparticle suspension. Since the analyte itself has specific functional groups complementary to the functional groups on the nanoparticle surface and able to enter into an affinity binding therewith, the analyte can be immobilized on the nanoparticle. The nanoparticles which are present in the suspension and on whose surface the analyte is immobilized can then be washed according to the invention, in which case the non-immobilized constituents of the sample are removed, and can after resuspension in an aqueous liquid be deposited on the MALDI sample carrier and investigated by spectrometry. However, there is also the possibility according to the invention of the nanoparticle suspension containing the bound analyte being deposited directly after binding of the analyte immediately on the MALDI sample carrier and being investigated by spectrometry.

The present invention thus provides a method with the aid of which it is possible to isolate the analyte from complex matrices and subsequently analyze it by MALDI-TOF MS without the need for the analyte to be separated from the nanoparticles again after immobilization onto the nanoparticles. The method of the invention thus has the crucial advantage compared with prior art methods that the analyte can be subjected to a direct MALDI-TOF investigation after isolation and immobilization together with the nanoparticles used according to the invention. Since separation of analyte and particle is unnecessary, no losses of analyte occur in this sample preparation step step.

It is possible by using the method of the invention to investigate a large number of different analytes, for example proteins, nucleic acids, etc. In particular, complexes of a plurality of proteins and/or peptides can be investigated, for example a biotinylated protein which binds a further protein and, in addition, a peptide in a complex. The analyte can be provided with a functional group which includes a plurality of constituents. For example, a protein may comprise as functional group an antibody and a receptor linked thereto. For example, a cDNA can be immobilized and used to look for proteins, for example transcription factors.

It has also surprisingly emerged that the matrix which is necessarily to be added for the MALDI-TOF analysis and which is vaporized during the analysis together with the analyte can be applied to the MALDI sample carrier either before the application of the nanoparticle suspension or together with the latter or after the application thereof.

The method of the invention can thus be carried out in a considerably simpler manner and in a substantially shorter time than conventional methods. The method of the invention advantageously also leads to distinctly lower limits of detection, to an improved signal/noise ratio and to good peak resolution. The MS spectra obtained using the method of the invention are distinguished for example by no interfering peaks occurring under usual MALDI-TOF conditions, for example laser intensity, and thus clearer results are obtained in the investigation.

The surprising advantages of the method of the invention are based in particular on the properties of the nanoparticles employed according to the invention. It is advantageous that the nanoparticles employed in the method of the invention do not in any way interfere with the MALDI analysis but in fact allow considerably improved analysis of the analyte compared with conventional sample preparation and MALDI methods. The nanoparticles used according to the invention have the following advantages in relation to the method of the invention:

The nanoparticles of the invention have a diameter of <150 nm which is very small compared with the particles normally used. They therefore have a comparatively very large surface/volume ratio and can accordingly bind a large amount of the analyte per unit mass. Owing to the very small diameter, embedding the nanoparticles in the MALDI matrix results in very homogeneous layers and surfaces, which is very important for the desorption process and the mass resolution. It is in fact possible to apply a plurality of layers of the particles to the sample carrier without interfering with the MALDI process, which leads to an additional increase in concentration of the analyte on the sample carrier.

Since the particles used according to the invention are preferably glass-like alkoxysilane condensates with a high degree of crosslinking, mobilization of the particles into the mass spectrometer is virtually precluded. Under normal MALDI conditions, for example laser intensity, therefore, no interfering peaks appear in the MS spectrum, in contrast to particles composed of synthetic polymers.

The nanoparticles used according to the invention can, owing to their high specific gravity, be removed rapidly by centrifugation and form very stable pellets. They can therefore be removed from liquid media rapidly and without loss, which in turn leads to a maximum analyte yield. The particle pellets can also be resuspended without difficulty, thus facilitating and expediting the MALDI sample preparation.

The nanoparticles used according to the invention are exceptionally chemically inert and mechanically stable. The particles do not swell in solvents. This means that the particles do not change their morphology, even if they are suspended in solvents several times over a lengthy period. The immobilized analytes can therefore be optimally separated from interfering substances such as non-specifically bound compounds with similar masses or substances interfering with the MALDI process, such as detergents and salts, through washing processes of any length.

The nanoparticles used according to the invention are equipped with surfaces which are modified in a variety of ways. The nanoparticles have different functional groups and thus permit the binding of different proteins. It is therefore possible by using the particles used according to the invention for a wide variety of analytes with complementary functional groups to be removed from complex mixtures and investigated directly with the aid of the MALDI-TOF MS method.

The nanoparticles used according to the invention show very good adhesion to conventional MALDI sample carriers. The particles can thus be used without difficulty in any MALDI instrument system and are independent of the system. MALDI mass spectrometric methods differ in particular in the nature of the mass analyzer used. The nanoparticles used according to the invention do not interfere with the matrix-assisted desorption and ionization process and can thus be employed in all conventional MALDI mass spectrometric methods for direct investigation of analytes after immobilization. The most frequently used mass analyzers are time-of-flight analyzers (TOF). The nanoparticles can be employed in linear and in reflected MALDI-TOF MS. In the reflection method this also makes possible so-called post-source decay investigation, i.e. the structure of the immobilized analyte can be determined by means of targeted fragment analysis.

The nanoparticles used according to the invention are therefore suitable in an outstanding manner for a so-called peptide mapping, because they do not interfere with the enzymatic digestion which is necessary for the peptide mapping and do not adversely affect the mass resolution either. It is also possible, in particular for such a peptide mapping, for the proteins to be tethered to the surface of the nanoparticles covalently by crosslinkers. It is thus possible to carry out stringent washing steps, which are necessary in particular with complex samples, without losses of analyte. Nanoparticles equipped with suitable antibodies are moreover suitable in a particular manner for diagnosis in human medicine and/or veterinary medicine, for example for characterizing tumors, BSE tests, etc. They provide a crucial time advantage compared with conventional methods, which is of interest in particular in infections where time is critical.

In connection with the present invention, an "analyte" means a substance for which the intention is to determine the nature and amount of its individual constituents and/or which is to be removed from mixtures. The analyte in particular takes the form of proteins, but also of other compounds, for example nucleic acids or carbohydrates and the like. In a preferred embodiment of the invention, the analyte is a protein, peptide, drug, pollutant, toxin, pesticide, antigen or a nucleic acid.

In connection with the present invention, a "protein" means a molecule which includes at least two amino acids which are connected together by an amide linkage. In the context of the present invention, therefore, a protein can also be a peptide, for example an oligopeptide, a polypeptide or a part, for example a protein domain. Such a protein may be of natural or synthetic origin. The protein may be modified by methods of genetic manipulation compared with the wild-type protein and/or contain unnatural and/or unusual amino acids. The protein may be derivatized compared with the wild-type form, for example have glycosylations, it may be truncated, it may be fused to other proteins or be connected to molecules of another type, for example to carbohydrates.

A "sample" means an aqueous or organic solution, emulsion, dispersion or suspension which comprises an analyte as defined above in isolated and purified form or as constituent of a complex mixture of different substances. The sample may be for example a biological fluid such as blood, lymph, tissue fluid, etc., i.e. a fluid which has been taken from a living or dead organism, organ or tissue. A sample may, however, also be a culture medium, for example a fermentation medium, in which organisms, for example microorganisms, or human, animal or plant cells have been cultivated. A sample for the purposes of the invention may, however, also be an aqueous solution, emulsion, dispersion or suspension of an isolated and purified analyte. A sample may have already been subjected to purification steps, but may also be in unpurified form. The "provision of a sample" may therefore mean both the obtaining of a sample as defined above, and the partial or complete purification of the sample or of the analyte after obtaining the sample.

In connection with the present invention, a "nanoparticle" means a particulate binding matrix which comprises a core with a surface which has functional groups able to bind complementary functional groups of the analyte covalently or non-covalently, with the analyte being immobilized on the nanoparticle. Nanoparticles have a size of <500 nm, preferably <150 nm. Nanoparticles are characterized by the core being chemically inert, in contrast to the surface. The "provision of nanoparticles" may thus mean both the preparation of the nanoparticles, i.e. the preparation of the cores using emulsion polymerization methods, sol-gel methods, etc., and the modification of the core surface by applying functional groups, and the use of finished nanoparticles which have already been prepared.

The "provision of a suspension of nanoparticles in an aqueous liquid" may mean both the suspension of nanoparticles in fluids, especially aqueous media, where appropriate using additional constituents, for example pH agents, suspending aids, etc., and the use of nanoparticle suspensions which have already been ready-prepared.

In connection with the present invention, a first functional group means a functional group of the analyte to be immobilized, the group being able to interact with a second functional group, i.e. a chemical group applied to the surface of the core, in such a way that affinity binding of a covalent or non-covalent nature can take place between the two binding partners in such a manner that the analyte is immobilized on the nanoparticle.

In a preferred embodiment of the present invention, the first functional group, i.e. the functional group of the analyte, is selected from the group consisting of carboxy groups, amino groups, thiol groups, biotin groups, Strep tag I groups, Strep tag II groups, His tag groups, Flag tag groups, antibodies against protein A, antibodies against protein G, biotinylated antibodies and biotinylated receptors. The receptors may be for example MHC proteins, cytokines, T-cell receptors such as the CD-8 protein and others. It is also possible to construct more complex layers. For example, an antibody may have a streptavidin group and a biotinylated antibody group and a protein group, the protein possibly being for example a receptor.

The second functional group, i.e. the functional group on the surface of the nanoparticle, is selected according to the invention from the group consisting of amino groups, carboxy groups, maleimido groups, avidin groups, streptavidin groups, neutravidin groups, metal chelate complexes, protein A units, protein G units, antibodies, receptor units or parts thereof. For specific solutions to problems it is also possible to immobilize antibodies or receptors as second functional group directly on the nanoparticle.

A nanoparticle used according to the invention thus has on its surface a second functional group which is linked covalently or non-covalently to a first functional group of an analyte to be immobilized, the first functional group being a group different from the second functional group. The two groups which bind together must be complementary to one another, i.e. able to enter into a covalent or non-covalent binding with one another.

If, for example, a carboxy group is used according to the invention as first functional group, the second functional group is an amino group. If, conversely, an amino group is used according to the invention as first functional group, the second functional group according to the invention is a carboxy group. If a thiol group is selected according to the invention as first functional group, the second functional group is according to the invention a maleimido group. If biotin groups and/or Strep tag I groups and/or Strep tag II groups are used according to the invention as first functional groups, the second functional group is an avidin group and/or a streptavidin group and/or a neutravidin group. If a thiol group is selected according to the invention as first functional group, the second functional group is according to the invention a maleimido group. If an antibody against protein A is employed according to the invention, protein A is employed according to the invention as second functional group. If an antibody against protein G is used according to the invention as first functional group, the second functional group is protein G.

The aforementioned first and/or second functional groups can be connected according to the invention with the aid of a spacer to the analyte to be immobilized, in particular the protein to be immobilized, or to the core, or be introduced by means of a spacer onto the core or into the analyte. The spacer thus serves on the one hand to maintain the distance between the functional group and the core or analyte, and on the other hand as carrier of the functional group. Such a spacer may represent according to the invention alkylene groups or ethylene oxide oligomers having 2 to 50 C atoms, which in a preferred embodiment is substituted and has heteroatoms. The spacer may be flexible and/or linear.

A preferred embodiment of the invention provides for the first functional groups to be a natural constituent of the analyte, in particular of a protein.

In a protein of medium size, i.e. a size of about 50 kDa with about 500 amino acids, there are about 20 to 30 reactive amino groups which are suitable in principle as functional groups for the immobilization. These are in particular amino groups at the N-terminal end of a protein. The amino groups and all lysine residues are also suitable for the immobilization. Arginine with its guanidium group is also suitable as functional group. Analytes such as nucleic acids contain for example carboxylic acid groups which can be used for the immobilization. The carboxylic acid groups in proteins by contrast must be activated.

A further preferred embodiment of the invention provides for the first functional groups being introduced into the analyte by means of methods of genetic manipulation, biochemical, enzymatic and/or chemical derivatization or chemical synthetic methods.

If the analyte is a protein, it is possible for example to introduce unnatural amino acids into the protein molecule by methods of genetic manipulation or during a chemical protein synthesis, for example together with spacers or linkers. Such unnatural amino acids are compounds which have an amino acid function and a radical R and are not defined by a naturally occurring genetic code, these amino acids particularly preferably having a thiol group. It is also possible to provide according to the invention for the modification of a naturally occurring amino acid, for example lysine, for example by derivatization of its side chain, in particular the primary amino group thereof, with the carboxylic acid function of levulinic acid.

In a further preferred embodiment of the present invention, functional groups can be introduced into a protein by modification thereof, in which case tags, i.e. labels, are attached to the protein, preferably at the C terminus or the N terminus. These tags may, however, also be disposed intra-molecularly. It is provided in particular that a protein is modified by attaching at least one Strep tag, for example a Strep tag I or Strep tag II or biotin. A Strep tag also means according to the invention functional and/or structural equivalents as long as they are able to bind streptavidin groups and/or its equivalents. The term "streptavidin" thus includes for the purposes of the present invention its functional and/or structural equivalents.

It is possible in a further embodiment of the invention for proteins which are to be analyzed by means of a MALDI-TOF method to be labeled with antibodies, especially antibodies against protein A or antibodies against protein G, by using conventional methods.

"Antibody" means a polypeptide which is essentially encoded by an immunoglobulin gene or immunoglobulin genes, or fragments thereof, which specifically bind(s) and recognize(s) an analyte (antigen). Known immunoglobulin genes include both the kappa, lambda, alpha, gamma, delta, epsilon and mu genes for the constant region and the innumerable genes for the variable immunoglobulin region. Antibodies exist for example as intact immunoglobulins or as a number of well-characterized fragments which are generated by cleavage with various peptidases. "Antibody" also means modified antibodies (e.g. oligomeric, reduced, oxidized and labeled antibodies). The term "antibody" used in the present description also includes antibody fragments which have been generated either by modification of whole antibodies or by means of de novo synthesis using DNA recombination techniques. The term "antibody" includes both intact molecules and fragments thereof, such as Fab, $F(ab')_2$ and Fv, which are able to bind the epitope determinants.

A preferred embodiment of the invention thus provides for proteins which are modified for example with unnatural amino acids, natural but unnaturally derivatized amino acids or specific Strep tags, or antibody-bound proteins, to be bound to nanoparticle surfaces having reactivity complementary thereto in such a way that a suitable specific, especially non-covalent, attachment of the proteins and thus an immobilization of the proteins on the surfaces takes place.

A further embodiment of the invention provides for the use in the method of the invention of nanoparticles which comprise a core which can be prepared from alkoxysilanes, preferably using a sol-gel method.

In connection with the present invention, a "core" means a chemically inert material which serves as support for the immobilized analyte. The core of the nanoparticles of the invention therefore preferably consists of alkoxysilane condensates which are additionally crosslinked and thus have a glass-like character. The cores of the nanoparticles used according to the invention have according to the invention a high specific gravity. A further embodiment of the invention provides for the specific gravity of the cores being increased by a cocondensation with heavy compounds, especially tungstates, etc., takes place during their preparation. The invention further provides for the core of the nanoparticles of the invention to have a diameter of <500 nm, in particular 30 nm to 400 nm, preferably 50 nm to 150 nm.

The surface of the core is characterized according to the invention by being modified by introduction of the complementary second functional groups which bind the first functional groups. The invention provides in particular for the functional groups to be introduced onto the surface of the core by using standard methods such as graft polymerization, silanization, chemical derivatization and similar suitable methods.

A preferred embodiment of the invention provides for the possibility of modifying the surface of the core by attaching additional functionalities.

The surface of the nanoparticles used in the method of the invention preferably has chemical compounds which prevent or reduce nonspecific adsorption of further analytes, especially further proteins, onto the nanoparticles. The surface particularly preferably has ethylene glycol oligomers.

There is also the possibility according to the invention for ion exchange functions to be tethered, separately or additionally, to the surface of the nanoparticles. In MALDI analysis, the salt content of the matrix is often a critical variable because addition of ions leads to suppression of ionization or to peak broadening, or that interfering peaks result. This problem can be averted with nanoparticles which have a high ion exchange capacity and thus fix interfering salts in the matrix. Nanoparticles with ion exchange function are suitable in particular for optimizing the MALDI analysis of nucleic acids because the latter can by this means be converted into a defined mass state.

The invention provides for the possibility that that the matrix which is necessarily added for the MALDI-TOF analysis and is vaporized during the analysis together with the analyte is applied either before the application of the nanoparticle suspension or together with the latter or after the application thereof to the MALDI sample carrier.

Matrix substances employed in MALDI mass spectrometry are low molecular weight compounds which firstly are able to absorb the wavelength of the laser employed for desorption and secondly are capable of efficient embedding of the analytes. Desorption and ionization is made possible only thereby. Ionization takes place mainly by ion transfer to the analyte, for example by protonation. Diverse compounds are used as matrix substances for different laser wavelengths and different classes of analytes. The compounds usually have aromatic groups. The matrices most frequently employed in the UV MALDI-TOF MS of proteins are 3,5-dimethoxycinnamic acid (sinapinic acid) or α-cyano-4-hydroxycinnamic acid. It is also possible in addition to use mixtures of these matrix compounds and so-called cationizers. These cationizers are in particular sodium, potassium or silver salts and make it possible for carbohydrates or synthetic polymers to ionize during the laser desorption.

The present invention also relates to nanoparticles which are used in the method of the invention for investigating an analyte, in particular a protein, by means of matrix-assisted laser desorption/ionization time-of-flight mass spectroscopy (MALDI-TOF MS).

The nanoparticles used according to the invention include a core with a surface which has different functional groups for affinity binding of complementary functional groups. Owing to the different surface modifications with different functional groups, the nanoparticles of the invention are suitable for the immobilization of a large number of analytes.

A preferred embodiment of the invention relates to nanoparticles whose surface is functionalized by attachment of amino groups. Nanoparticles of this type are particularly suitable according to the invention for the covalent immobilization of at least one protein with activated carboxy groups and/or at least one nucleic acid and for the removal thereof from a complex mixture and direct investigations by means of MALDI-TOF MS.

A further preferred embodiment relates to nanoparticles whose surface has carboxy groups. Nanoparticles of this type are particularly suitable for the covalent immobilization of at least one protein with freely accessible amino groups and for the removal thereof from a complex mixture and direct investigation by means of MALDI-TOF MS.

A further preferred embodiment of the invention relates to nanoparticles whose surface has maleimido groups. Nanoparticles of this type are particularly suitable for the covalent immobilization of at least one protein with thiol groups and for the removal thereof from a complex mixture and direct investigation by means of MALDI-TOF MS.

A further embodiment of the invention provides nanoparticles whose surface has avidin groups, streptavidin groups and/or neutravidin groups. Nanoparticles of these types are particularly suitable for the immobilization of proteins with biotin groups and/or Strep tag groups and for the removal thereof from a complex mixture and direct investigation by means of MALDI-TOF MS.

A further embodiment of the invention relates to nanoparticles whose surface has protein A units. Nanoparticles of this type are particularly suitable for the immobilization of at least one antibody and/or one antibody-bound protein and for the removal thereof from a complex mixture and direct investigation by means of MALDI-TOF MS.

Yet a further embodiment of the present invention relates to nanoparticles whose surface has protein G units. Nanoparticles of this type are particularly suitable for the immobilization of antibodies and/or antibody-bound proteins and for the removal thereof from a complex mixture and direct investigation by means of MALDI-TOF MS.

The nanoparticles of the invention include a core which consists of a chemically inert material, preferably of glass-like crosslinked alkoxysilane condensates, the core preferably being prepared by sol-gel synthesis using alkoxysilanes. The nanoparticles of the invention have a high specific gravity owing to the composition of the cores. This high weight of the cores can be increased according to the invention through additional cocondensation with heavy compounds, especially with tungstates, during the preparation of the cores.

A further preferred embodiment of the invention further provides for the nanoparticles which have different functional groups on their surface to have different dye labels. The different dye labels facilitate on the one hand the distinguishing of the different surface modifications, i.e. the different functional groups, of the particles of the invention. On the other hand, the dye labels facilitate the manipulation of the nanoparticles of the invention, which has advantageous effects especially in centrifugations, because even very small pellets can easily be recognized.

The present invention also relates to a ready-to-use nanoparticle suspension which comprises at least one nanoparticle species of the invention, i.e. nanoparticles with one of the aforementioned specific surface modifications, in an aqueous medium, where appropriate together with further additions, for example pH agents, suspending aids, etc. Such nanoparticle suspensions can be employed directly for sample preparation, i.e. isolation and purification of an analyte, for subsequent MALDI-TOF analysis.

In a further embodiment, the present invention also relates to kits which comprise at least one of the aforementioned nanoparticle species, i.e. nanoparticles with one of the aforementioned functional group, but preferably a plurality of these nanoparticle species in powder form and/or as suspension. Such kits can be employed for sample preparation for a large number of different analytes for subsequent MALDI-TOF analysis.

The analyte-carrying nanoparticles can in a particularly preferred embodiment be applied not just once to the MALDI sample carrier. A multiple application, which is preferred according to the invention, in particular 2×–100×, preferably 10×–20×, alternating with a drying step and/or a matrix deposition, allows the analyte to be concentrated on the sample carrier without the particles having an adverse effect on the MALDI process.

Besides the analyte it is possible for further peptides and/or proteins to be bound deliberately to the nanoparticles, which permit internal calibration of the molecular weight (peak position) and/or of the concentration (peak height).

Further advantageous embodiments of the invention are evident from the dependent claims.

BRIEF DESCRIPTION OF THE DRAWINGS

The invention is explained further by means of the following examples and figures.

DESCRIPTION OF EXEMPLARY EMBODIMENTS

Figure 3:
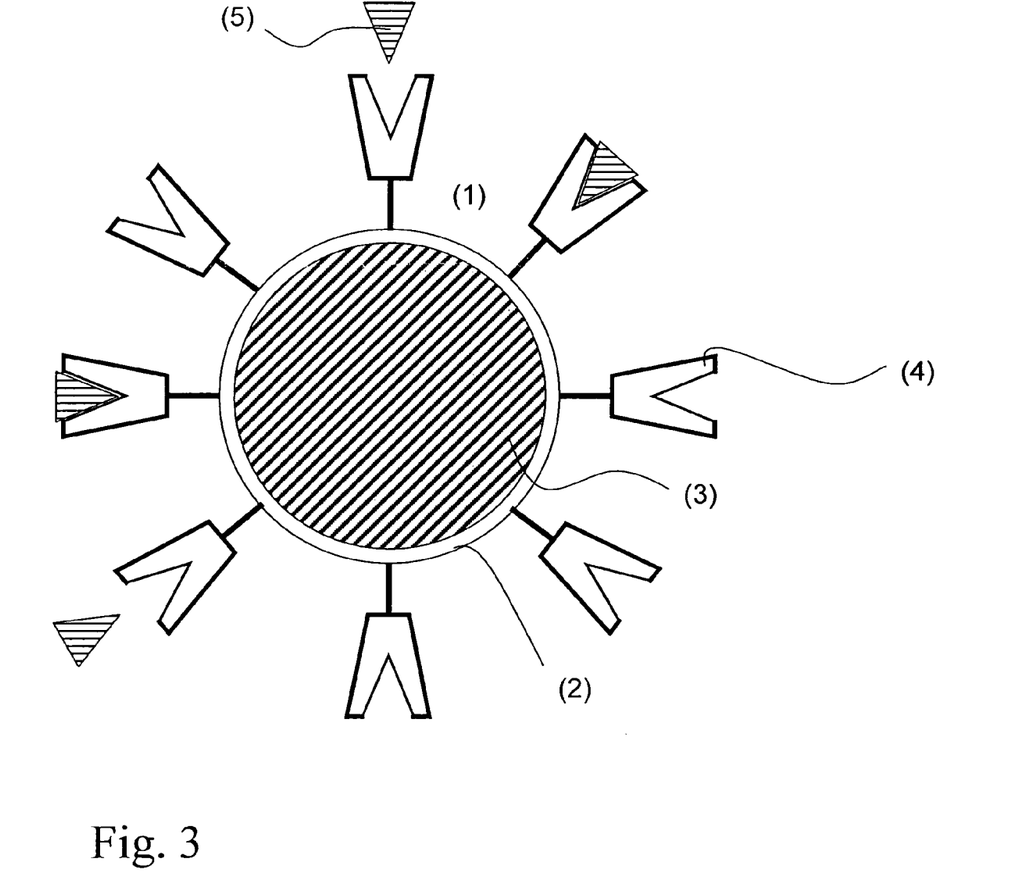
FIG. 3 is a schematic representation of the inventive nanoparticle.

FIG. 3 schematically shows a nanoparticle 1 according to the invention. The nanoparticle 1 has a core 3 with a surface 2 that has functional groups for affinity binding 4 of complementary functional groups of at least one analyte 5.

Figure 4:
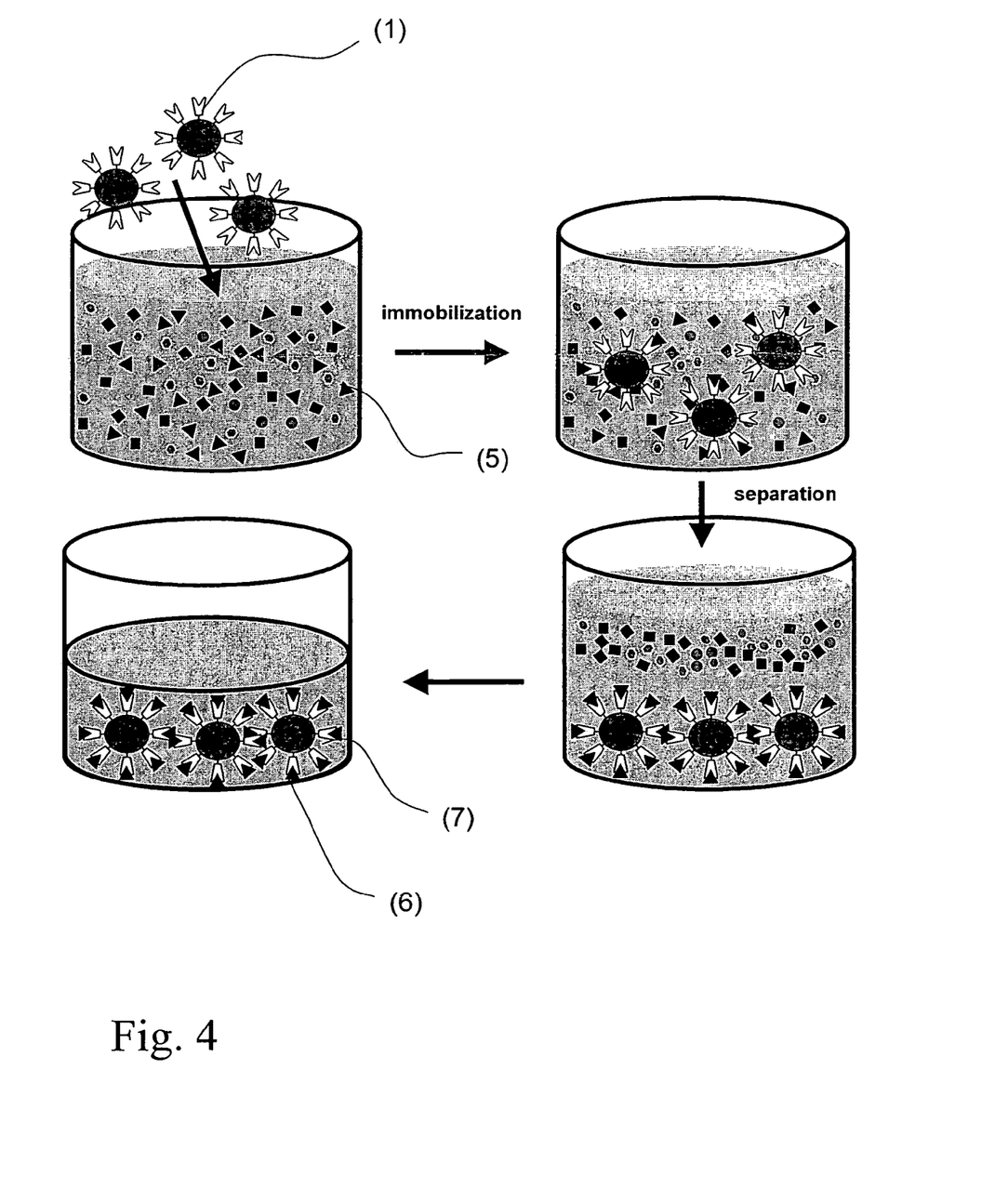
FIG. 4 schematically shows the steps of a method for investigating an analyte.

FIG. 4 schematically shows the steps of a method for investigating at least one analyte 5 by means of MALDI-TOF mass spectrometry. These steps include providing a sample with the analyte 5, providing nanoparticles 1 according to the present invention in a suspension in an aqueous liquid, adding the nanoparticle suspension, and the final image shows the suspension 6 containing the nanoparticles with the bound analyte 7.

Figure 5:
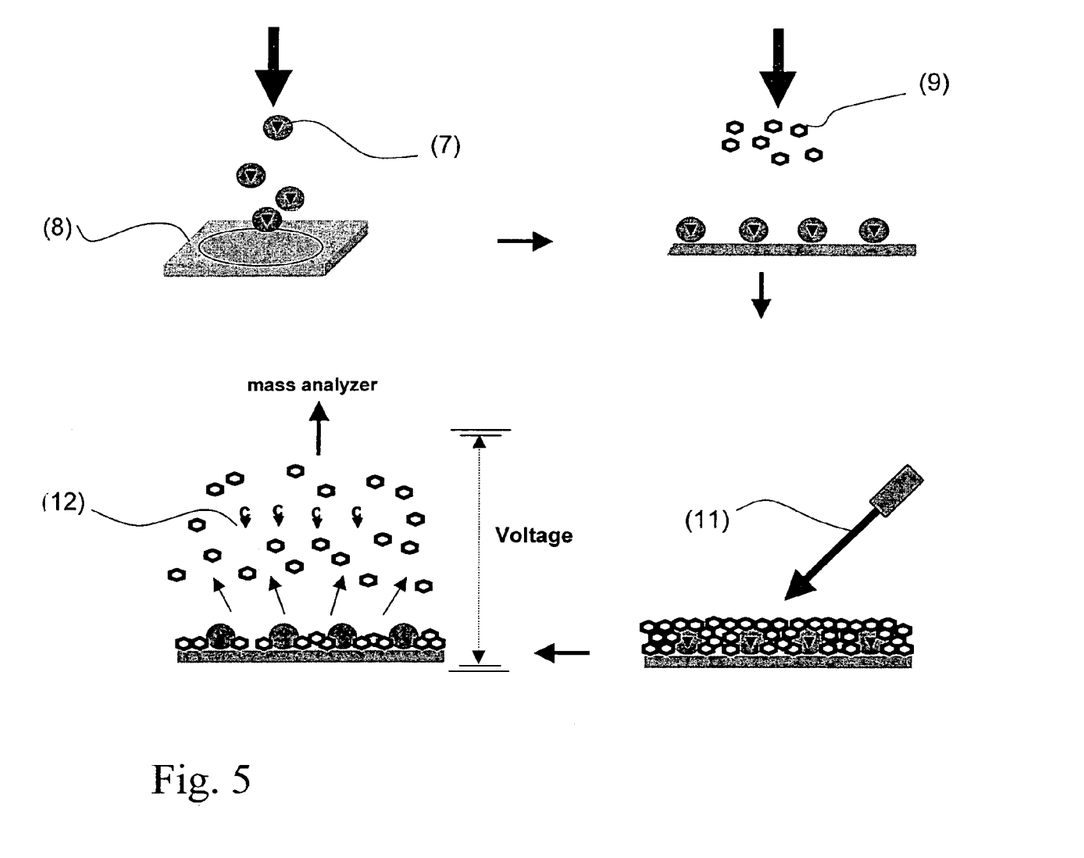
FIG. 5 schematically shows further steps of the method.

FIG. 5 schematically depicts the further steps comprising the deposition of the suspension containing the bound analyte 7 on a MALDI sample carrier 8, the spectrometric investigation of the analyte with MALDI-TOF mass spectrometry, utilizing matrix 9 and a laser 11 for desorption/ionization and mass spectrometry of the charged analyte 12.

EXAMPLE 1

Preparation of Nanoparticulate Cores

Silica Carrier 12 mmol of tetraethoxysilane and 90 mmol of $NH_3$ were added to 200 ml of ethanol. The mixture was stirred at room temperature for 24 hours and then the particles which had formed were purified by multiple centrifugation. This resulted in 650 mg of silica particles with an average particle size of 125 nm.

EXAMPLE 2

Surface Modification of the Cores 2.1 Amino-Functionalized Surface

A 1% by weight aqueous suspension of the cores obtained in example 1 was mixed with 10% by volume of 25% ammonia. 20% by weight of aminopropyltriethoxysilane, based on the cores, were added and the mixture was stirred at room temperature for one hour. The particles were purified by multiple centrifugation. The resulting particles have functional amino groups on their surface (zeta potential in 0.1 M acetate buffer: +35 mV).

2.2 Pegylated Surface 1 mg of amino-functionalized particles (example: 2.1) are suspended in 1 ml of 10 mM phosphate buffer (pH: 7.0). Subsequently, up to 1 mg of heterofunctional polyethylene glycols such as mPEG-succinimidyl propionate, t-Boc-NH-PEG-succinimidyl propionate, maleimido-PEG-succinimidyl propionate or mixtures thereof are added, and the mixture is shaken at room temperature for 3 hours. If protective groups are present on the surface they are removed by treatment with 1% trifluoroacetic acid for 2 hours. The particles are washed twice with 1 ml of 10 mM phosphate buffer (pH: 7.0).

These surfaces are suitable for avoiding nonspecific attachment of proteins.

If these surfaces have amino groups after deblocking of the protective groups, they can be used further in examples 2.6/2.7.

2.3 Carboxy-Functionalized Surface

Firstly a 2% by weight suspension of amino-functionalized cores in tetrahydrofuran was prepared. 260 mg of succinic anhydride were added to 10 ml of this solution. Ultrasound treatment for 5 minutes was followed by stirring at room temperature for one hour. The cores were then purified by multiple centrifugation. The resulting silica cores have functional carboxy groups (zeta potential in 0.1 M acetate buffer: −35 mV) on their surface and have an average particle size of 170 nm.

2.4 Nitrilotriacetic Acid (NTA) Surface 10 mg of carboxy-modified cores were washed twice with 1 ml of acetonitrile (MeCN) and then taken up in 1 ml of MeCN. To this were added 10 µmol of dicyclohexylcarbodiimide and 10 µmol of N-hydroxysuccinimide. This was followed by shaking at room temperature for two hours. Washing was then carried out once with 1 ml of cyclohexane and once with 1 ml of MeCN. The particles were then taken up in 1 ml of MeCN. 4 µmol of N,N-biscarboxymethyl-L-lysine were added thereto and shaken at room temperature for three hours. This was followed by washing once with 1 ml of acetonitrile and twice with 1 ml of 10 mM phosphate buffer (pH 7.0).

This reaction firstly increases the density of the functional carboxy groups and secondly $Ni^{2+}$ ions can be bound by complexation with this surface. This surface is then able to bind proteins modified with His tags.

2.5 Thiol Surface 10 mg of carboxy-modified cores were washed twice with 1 ml of acetonitrile (MeCN) and then taken up in 1 ml of MeCN. 10 µmol of dicyclophexylcarbodiimide and 10 µmol of N-hydroxysuccinimide were added thereto and then shaken at room temperature for two hours. This was followed by washing once with 1 ml of cyclohexane and once with 1 ml of MeCN. The cores were then taken up in 1 ml of MeCN. 500 µg of cysteine were added thereto and shaken at room temperature for three hours. This was followed by washing once with 1 ml of acetonitrile and twice with 1 ml of 10 mM phosphate buffer (pH 7.0).

This surface is particularly suitable for immobilizing proteins via disulfide bridges.

2.6 Maleimido-Activated Surface

500 µg of amino-functionalized cores were resuspended in 1 ml of 10 mM phosphate buffer (pH 7.0). 1.25 µmol of sulfo-succinimidyl 4-(N-maleimidomethyl)cyclohexane-1- carboxylate were added thereto and shaken at room temperature for one hour. This was followed by washing once with cold 10 mM phosphate buffer (pH 7.0), and the cores were taken up in 1 ml of 0.1 M phosphate buffer (pH 7.0).

2.7 Iodoacetyl-Activated Surface

500 µg of amino-functionalized cores were resuspended in 1 ml of 10 mM phosphate buffer (pH 7.0). 1.25 µmol of succinimidyl 4-(iodoacetyl)aminobenzoate were added thereto and shaken at room temperature for one hour. This was followed by washing once with cold 0.1 M phosphate buffer (pH 7.0), and the cores were taken up in 1 ml of 10 mM phosphate buffer (pH 7.0).

These surfaces of 2.8 and 2.9 are suitable for coupling on proteins having free thiol groups.

2.8 Streptavidin-Modified Particles

15 µg of streptavidin were added to 1 ml of MES buffer (pH 5.0). To this were added 500 µg of carboxy-functionalized nanoparticles and 100 nmol of EDC. The mixture was shaken at room temperature for 3 h, and the particles were removed by centrifugation and washed twice with 1 ml of PBS buffer. After suspension in PBS, the particles have a size of 200 nm and have 3% by weight of streptavidin on their surface. This method can also be used to immobilize other proteins, for example streptactin and protein G, on the surface.

EXAMPLE 3

MALDI

Immobilization and direct MALDI MS detection of huMIF on streptavidin-conjugated silica nanoparticles.

Figure 1:
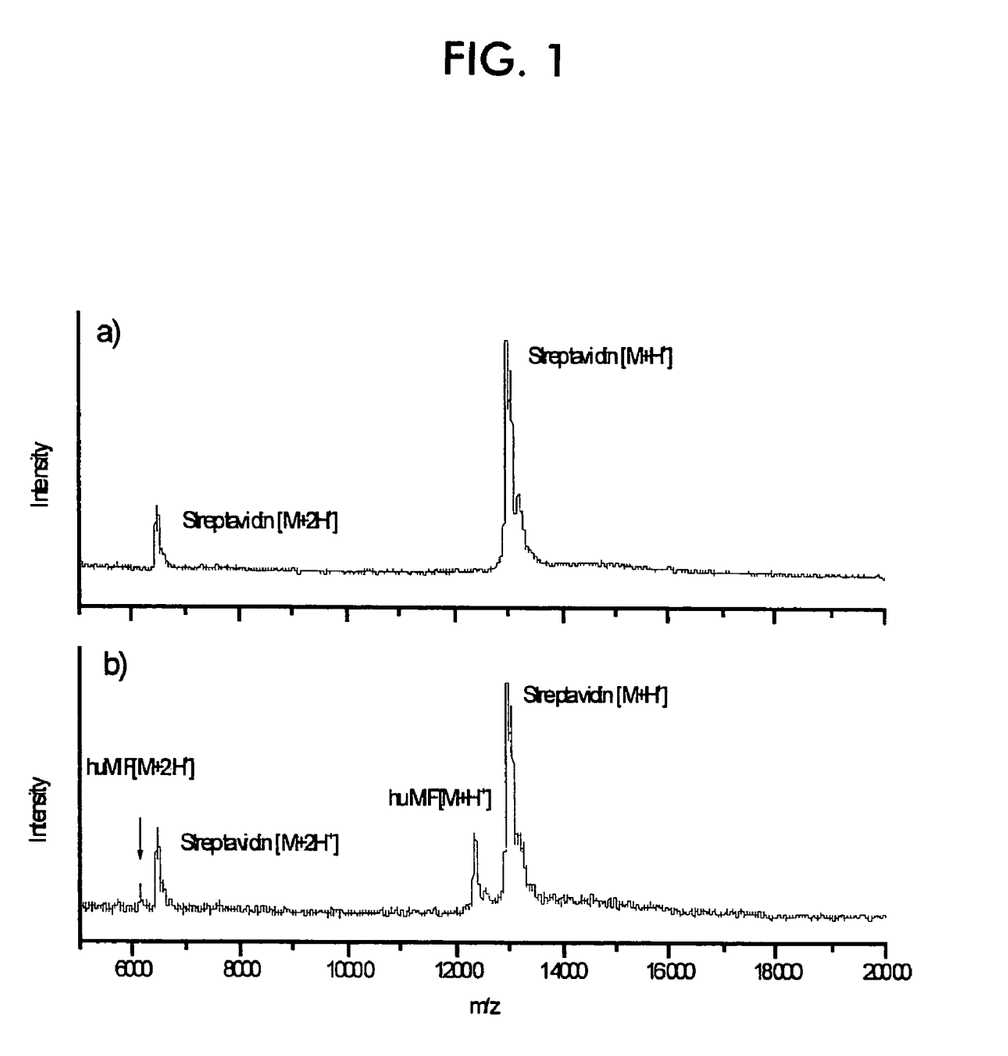
FIG. 1 shows two mass spectra.

FIG. 1a) shows a mass spectrum of nanoparticles without immobilization of proteins. The spectrum shows only peaks of the streptavidin monomer. FIG. 1b) shows a mass spectrum of nanoparticles after they have been put into a solution of huMIF and biotinylated anti-huMIF antibody and then washed several times with buffer solutions. Unambiguous signals of huMIF are obtained. This means that huMIF was specifically bound to the nanoparticles and can be detected directly thereon.

Example of the concentration of nanoparticles on MALDI sample carriers.

Figure 2:
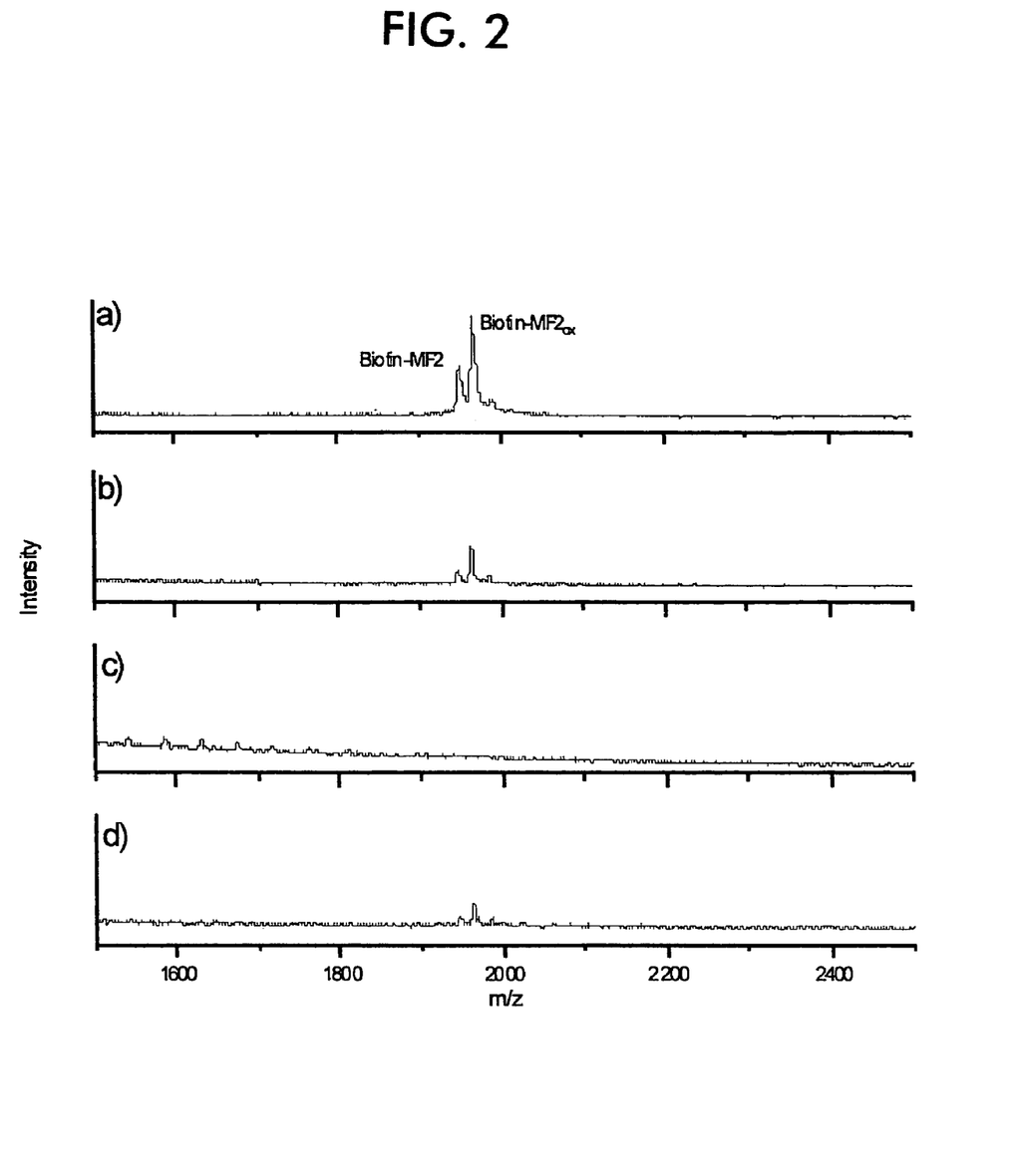
FIG. 2 shows further mass spectra.

FIG. 2 demonstrates the concentration of silica nanoparticles on MALDI sample carriers. FIGS. 2(a)–(c) show mass spectra of (a) 50 pmol, (b) 5.0 pmol, and (c) 0.50 pmol of biotinylated MF2 immobilized on in each case 25 µg of silica nanoparticles. (a) and (b) show peaks with diminishing intensity corresponding to the absolute amount of analyte on the sample carriers. Signals from the analyte are no longer obtained in (c). FIG. 2(d) shows a mass spectrum of the same silica nanoparticles from (c). In this case, 250 µg of these particles were loaded by repeated application to the sample carrier, so that a total of 5.0 pmol of the analyte—i.e. ten times the amount in (c)—is present on the target. The mass spectrum shows peaks with almost the same signal-to-noise ratio as the mass spectrum from (b), in which likewise 5.0 pmol of analyte were absolutely applied to the target.

The invention claimed is:

1. A method for investigating at least one analyte by means of matrix-assisted laser desorption/ionization mass spectrometry (MALDI MS), comprising the steps of: providing a sample with the analyte having first functional groups; providing nanoparticles which comprise a core with a diameter of from 30 to 400 nm and a surface which has complementary second functional groups which bind the first functional groups; providing a suspension of the nanoparticles in an aqueous liquid; adding the sample containing the at least one analyte to the nanoparticle suspension, or adding the suspension to the sample containing the analyte; permitting affinity binding of the analyte to the nanoparticles; subsequently depositing the suspension containing the bound analyte on a MALDI sample carrier; and investigating the analyte spectrometrically.

2. The method as claimed in claim 1, where the MALDI MS method is matrix-assisted laser desorption/ionization time-of-flight mass spectrometry (MALDI-TOF MS).

3. The method as claimed in claim 1, where the first functional groups are selected from the group consisting of carboxy groups, amino groups, thiol groups, biotin groups, His tag groups, Flag tag groups, Strep tag I groups, Strep tag II groups, histidine tag groups, Flag tag groups, antibodies against protein A, antibodies against protein G, biotinylated antibody and biotinylated receptors.

4. The method as claimed in claim 1, where the complementary second functional groups binding the first functional groups are selected from the group consisting of amino groups, carboxy groups, maleimido groups, avidin groups, streptavidin groups, neutravidin groups, metal chelate complex, protein A units, protein G units, antibodies, receptor units or parts thereof.

5. The method as claimed in claim 1, where the first functional groups are a natural constituent of the analyte.

6. The method as claimed in claim 1, including introducing the first functional groups into the analyte by means of methods of genetic manipulation, biochemical, enzymatic and/or chemical derivatization or chemical synthetic methods.

7. The method as claimed in claim 1, where the cores are prepared from alkoxysilanes.

8. The method as claimed in claim 1, where the cores are prepared with a diameter of from 50 nm to 150 nm.

9. The method as claimed in claim 1, including attaching the complementary second functional groups binding the first functional groups to the surface of the cores by means of graft polymerization, silanization, chemical derivatization and similar suitable methods.

10. The method as claimed in claim 1, including modifying the surface of the core by attaching additional functionalities.

11. The method as claimed in claim 10, including attaching chemical compounds to the surface of the core to prevent or reduce nonspecific adsorption of further proteins.

12. The method as claimed in claim 10, including attaching ethylene glycol oligomers to the surface of the core.

13. The method as claimed in claim 10, including attaching an ion exchange function to the surface of the core.

14. The method as claimed in claim 1, including removing the nanoparticles from the sample-containing suspension after binding of the analyte by means of at least one centrifugation and at least one washing step and resuspending the nanoparticles.

15. The method as claimed in claim 14, including configuring the nanoparticles at 15 000 g for 10 minutes.

16. The method as claimed in claim 14, including washing the nanoparticles with low-concentration buffer systems, deionized water, organic solvents or supercritical $CO_2$.

17. The method as claimed in claim 1, including loading a matrix employed in the course of a MALDI-TOF MS method onto the MALDI sample carrier before or after deposition of a nanoparticle-containing suspension or together therewith.

18. The method as claimed in claim 1, including applying the analyte-carrying nanoparticles more than once to the MALDI sample carrier.

19. The method as claimed in claim 1, where peptides or proteins are bound, besides the analyte, to the nanoparticles for internal calibration of the molecular weight or of the concentration.

20. The method as claimed in claim 1 for carrying out bombardment of a sample with electrons (BSE) tests, for tumor diagnosis and for the diagnosis of infectious diseases.

21. A nanoparticle for investigating an analyte by means of matrix-assisted laser desorption/ionization mass spectroscopy (MALDI MS), comprising a core with a diameter of from 30 to 400 nm and a surface which has functional groups for affinity binding of complementary functional groups of at least one analyte and thus for immobilization of the at least one analyte.

22. A nanoparticle as claimed in claim 21, where the surface has amino groups.

23. A nanoparticle as claimed in claim 22, suitable for the immobilization of at least one protein with activated carboxy groups and/or of at least one nucleic acid and for the removal thereof from a complex mixture and direct investigation by means of MALDI MS.

24. A nanoparticle as claimed in claim 21, where the surface has carboxy groups.

25. A nanoparticle as claimed in claim 24, suitable for the covalent immobilization of at least one protein with freely accessible amino groups and for the removal thereof from a complex mixture and direct investigation by means of MALDI MS.

26. A nanoparticle as claimed in claim 21, where the surface has maleimido groups.

27. A nanoparticle as claimed in claim 26, suitable for the covalent immobilization of at least one protein with thiol groups and for the removal thereof from a complex mixture and direct investigation by means of MALDI MS.

28. A nanoparticle as claimed in claim 21, where the surface has avidin groups, streptavidin groups and/or neutravidin groups.

29. A nanoparticle as claimed in claim 28, suitable for the immobilization of at least one protein with biotin groups and/or Strep tag groups and for the removal thereof from a complex mixture and direct investigation by means of MALDI MS.

30. A nanoparticle as claimed in claim 21, where the surface has protein A units.

31. A nanoparticle as claimed in claim 30, suitable for the immobilization of at least one antibody and/or one antibody-bound protein and for the removal thereof from a complex mixture and direct investigation by means of MALDI MS.

32. A nanoparticle as claimed in claim 21, where the surface has protein G units.

33. A nanoparticle as claimed in claim 32, suitable for the immobilization of at least one antibody and/or one antibody-bound protein and for the removal thereof from a complex mixture and direct investigation by means of MALDI MS.

34. A nanoparticle as claimed in claim 21, where the core consists of a chemically inert material.

35. A nanoparticle as claimed in claim 34, where the core consists of crosslinked alkoxysilane condensates.

36. A nanoparticle as claimed in claim 21, where the core can be prepared from alkoxysilanes.

37. A nanoparticle as claimed in claim 36, where the core can be prepared by cocondensation with heavy compounds.

38. A nanoparticle as claimed in claim 37, where the core can be prepared by cocondensation with tungstates.

39. A nanoparticle as claimed in claim 21, where the nanoparticle has a size of from 50 nm to 150 nm.

40. A nanoparticle as claimed in claim 21, where the nanoparticle has a dye label.

41. A nanoparticle suspension comprising at least one nanoparticle as claimed in claim 21 in an aqueous medium.

42. A kit comprising at least one nanoparticle as claimed in claim 21 in powder form and/or at least one nanoparticle suspension comprising at least one of the nanoparticles in an aqueous medium.

* * * * *